(12) United States Patent
Iwata

(10) Patent No.: US 7,169,300 B2
(45) Date of Patent: Jan. 30, 2007

(54) FRACTIONATING APPARATUS

(75) Inventor: Yosuke Iwata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/030,393

(22) Filed: Jan. 5, 2005

(65) Prior Publication Data
US 2005/0147536 A1 Jul. 7, 2005

(30) Foreign Application Priority Data
Jan. 6, 2004 (JP) ............................. 2004-000779

(51) Int. Cl.
B01D 15/08 (2006.01)

(52) U.S. Cl. ................... 210/198.2; 210/656; 210/101; 422/70; 250/288

(58) Field of Classification Search .................. 422/70; 250/288; 436/161, 173; 210/101, 198.2, 210/656
See application file for complete search history.

(56) References Cited

U.S. PATENT DOCUMENTS

| | | | | |
|---|---|---|---|---|
| 4,977,785 | A * | 12/1990 | Willoughby et al. | 73/863.12 |
| 5,477,048 | A * | 12/1995 | Nakagawa et al. | 250/288 |
| 5,674,288 | A * | 10/1997 | Knapp et al. | 623/11.11 |
| 5,690,828 | A * | 11/1997 | Clay et al. | 210/634 |
| 6,462,334 | B1 * | 10/2002 | Little et al. | 250/281 |
| 6,707,037 | B2 * | 3/2004 | Whitehouse | 250/288 |
| 6,709,632 | B2 * | 3/2004 | Nakagawa et al. | 422/54 |
| 6,800,849 | B2 * | 10/2004 | Staats | 250/288 |
| 6,803,568 | B2 * | 10/2004 | Bousse et al. | 250/288 |
| 6,812,458 | B2 * | 11/2004 | Gregori et al. | 250/288 |
| 6,977,369 | B2 * | 12/2005 | Yamaguchi et al. | 250/281 |
| 2002/0187073 | A1 * | 12/2002 | Moon et al. | 422/70 |
| 2004/0113068 | A1 * | 6/2004 | Bousse et al. | 250/288 |
| 2004/0238427 | A1 * | 12/2004 | Maruyama et al. | 210/198.2 |
| 2005/0147536 | A1 * | 7/2005 | Iwata | 422/100 |
| 2005/0158215 | A1 * | 7/2005 | Iwata et al. | 422/101 |

FOREIGN PATENT DOCUMENTS

| JP | 5-256749 | 10/1993 |
|---|---|---|
| JP | 3099866 | 12/2003 |

OTHER PUBLICATIONS

Machine Translation of Japan Patent No. 3099866, pp. 1-2 of claims and pp. 1-5 of detailed description.*
U.S. Appl. No. 11/030,394, filed Jan. 5, 2005, Iwata et al.
The Application of Multi-used Drip Tube in the Micro-Chemical Experiment, Hu Mancheng, Middle School Chemical Education Reference, 7th of 1994. (Discussed in English translation of Office action).

* cited by examiner

Primary Examiner—Ernest G. Therkorn
(74) Attorney, Agent, or Firm—Rankin, Hill, Porter & Clark LLP

(57) ABSTRACT

A tip portion of a probe has a triple tube structure in which a fused silica capillary on the innermost side, a capillary made of FEP outside the fused silica capillary, and a stainless pipe on the outermost side are disposed coaxially. An eluate from a liquid chromatograph flows through the innermost flow passage, a matrix solution flows through the flow passage between the fused silica capillary and the FEP capillary, and a rinsing solution or air flows through the flow passage between the FEP capillary and the pipe.

4 Claims, 2 Drawing Sheets

FRACTIONATING APPARATUS

BACKGROUND OF THE INVENTION

1. Field of the Invention

The present invention relates to a fractionating apparatus having a probe for dripping a sample liquid fed from a liquid feed mechanism such as an HPLC (High Performance Liquid Chromatograph), or the sample liquid with an additive agent, as a liquid droplet from a tip portion of the probe onto a plate such as a microplate or sample plate, and preparing a sample to be analyzed with MALDI-TOF-MS (Matrix Assisted Laser Desorption Ionization Time-Of-Flight Mass Spectrometry) or FT-IR (Fourier Transform Infrared Spectrophotometer).

2. Description of the Related Art

In the related art, when a sample liquid such as eluate from the liquid chromatograph is fractionated and captured on a sample plate for an analyzer of MALDI-TOF-MS or the like, for example, the sample liquid is automatically dripped and fractionated from the probe onto the sample plate. Usually, the fractionating apparatus has an X-Y stage and a Z stage, in which the sample liquid is fractionated and captured by moving the sample plate in the horizontal and vertical directions. In dripping the sample liquid, the sample plate is raised to approach a lower end face of the probe, and the sample liquid emerging from the lower end face of the probe is contacted with and moved onto the sample plate.

Such probe of the fractionating apparatus is made of stainless, fused silica, or PEEK (polyether ether ketone).

However, since stainless, fused silica or PEEK used as the material of the probe has poor hydrophobic property, when a liquid having great surface tension such as water is flowed, a liquid droplet may rise up the outside surface of the probe, depending on the surface tension of the sample liquid to be dripped. As a result, if a sample liquid amount reaches a uniform amount essentially fractionated on the sample plate, and the sample plate is raised to approach the lower end face of the probe, the liquid droplet does not make contact with the sample plate and is not fractionated, so that the amount of fractionation is varied at each spot.

In order to solve the above-mentioned problems, it is common practice that the material of the probe is fused silica capillary, and Teflon (registered trademark) is coated to increase the hydrophobic property on the surface of the capillary. However, a special coating technique is needed to coat Teflon on the surface of the probe, and the surface of the probe coated with Teflon does not withstand the service for a long time due to a life of coating.

SUMMARY OF THE INVENTION

Thus, it is an object of the invention to provide a fractionating apparatus that can uniformly drip the sample liquid droplet on the sample plate stably for a long time.

The present invention provides a fractionating apparatus comprising: a probe for dripping a sample liquid fed from a liquid feed mechanism such as a liquid chromatograph as a liquid droplet from a tip portion of the probe onto a plate. In the fractionating apparatus, the tip portion of the probe has a single or multiple tube structure, and an outermost tube of the tube in contact with the liquid droplet is made of a hydrophobic material.

In a preferred form, the tip portion of the probe comprises a double tube structure with a central tube for feeding the sample liquid and an additive agent supply tube coaxial with the central tube and disposed outside the central tube, wherein the additive agent supply tube is made of a hydrophobic material.

A preferable example of the hydrophobic material is fluororesin. As such fluororesin, typically ethylene tetrafluoride resin (PTFE) such as Teflon (registered trademark), and various modified fluororesins may be employed. Such modified fluororesins include ethylene tetrafluoride propylene hexafluoride (FEP), ethylene tetrafluoride perfluoro alkoxy copolymer resin (PFA), and ethylene tetrafluoride ethylene copolymer resin (ETFE) such as Tefzel (registered trademark).

The sample suitably prepared using the fractionating apparatus of the invention is analyzed with the MALDI-TOF-MS or FT-IR.

In the fractionating apparatus of the invention, since the outermost tube in contact with the sample liquid droplet to be dripped at the tip portion of the probe is made of the hydrophobic material, the liquid droplet is prevented from adhering to an outside surface of the tip portion of the probe, whereby the uniform liquid droplet is fractionated on the sample plate.

Also, the tube made of the hydrophobic material requires no special coating technique, because the tube itself is made of the hydrophobic material but is not coated with the hydrophobic material, whereby the fractionating apparatus is produced cheaply.

DETAILED DESCRIPTION OF THE INVENTION

Figure 1:
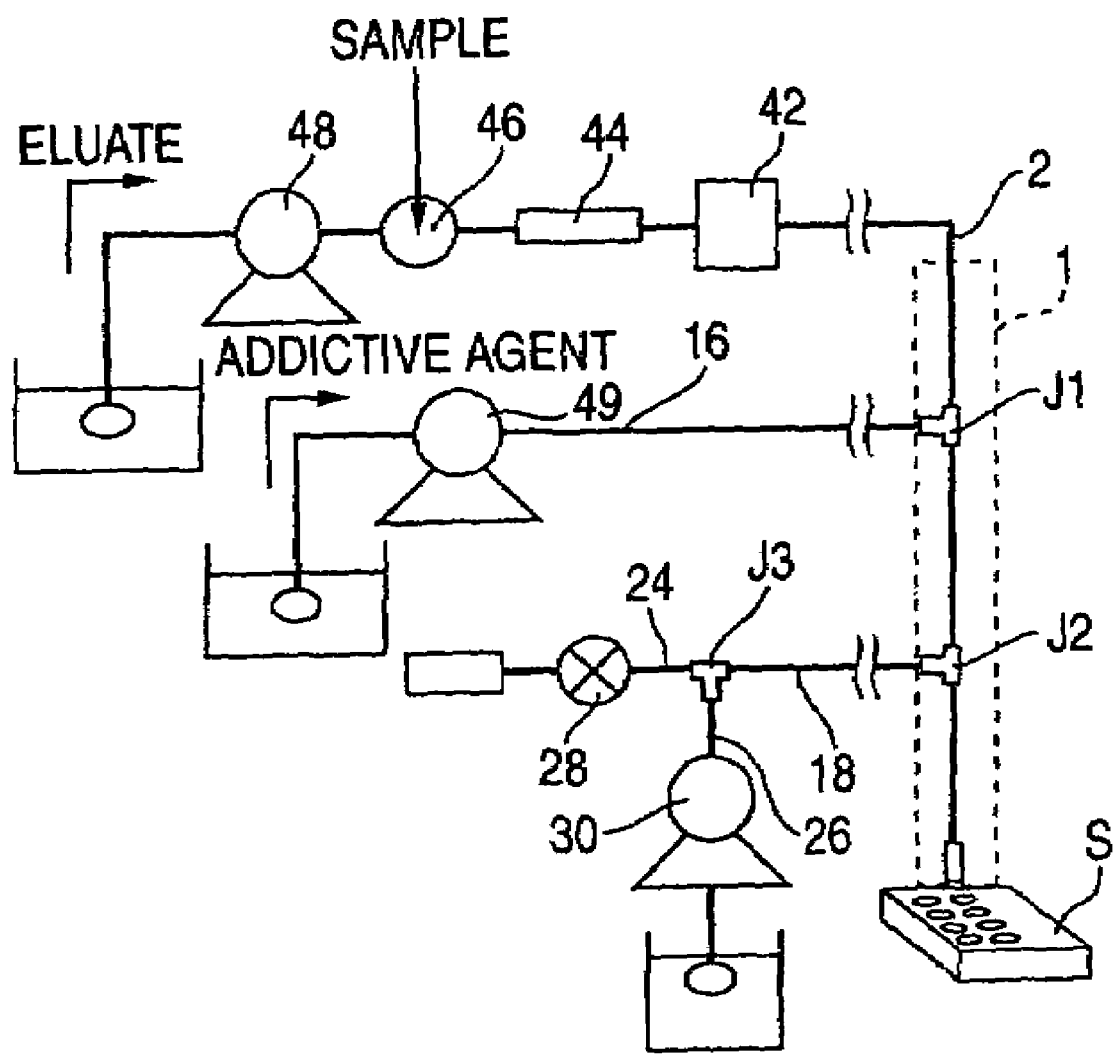
FIG. 1 is a schematic view showing a liquid chromatograph with a fractionating apparatus according to one embodiment of the invention.

FIG. 1 is a schematic view showing a liquid chromatograph with a fractionating apparatus according to one embodiment of the invention.

The high performance liquid chromatograph comprises a pump 48 for feeding eluate, an injector 46 for injecting a sample, a column 44 for separating the sample constituents, and a detector 42, which are disposed along the flow passage of eluate. A probe 1 for dripping the liquid droplet is connected via a capillary 2 downstream of the detector 42.

The probe 1 comprises the T-type three-way joints J1 and J2, in which an upstream joint J1 connects the capillary 2 for feeding the eluate and a tube 16 for feeding a matrix solution, and a downstream joint J2 connects the capillary 2 and a tube 18 for supplying the air and acetone as rinsing solution, in which a tip portion on the exit side of the probe 1 forms a triple tube structure.

The eluate is fed by the pump 48, and a sample is injected from the injector 46. The sample injected from the injector 46 is separated for each constituent by the column 44, and detected by the detector 42. The eluate is passed through the capillary 2, dripped from the probe 1 onto a sample plate S and captured.

One example of additive agent added to the eluate is a matrix solution. Examples of the matrix include nicotinic acid, 2-pyrazine carboxylic acid, sinapic acid (3,5-dimethoxy-4-hydroxycinnamic acid), 2,5-dihydroxybenzoic acid, 5-methoxysalicylic acid, α-cyano-4-hydroxycinnamic acid (CHCA), 3-hydroxypicolinic acid, diaminonaphthalene, 2-(4-hydroxyphenylazo) benzoic acid, dislanol, succinic acid, 5-(trifluoromethyl) uracil, and glycerin.

The rinsing solution for dissolving the matrix may be an organic solvent such as acetone or acetonitrile.

Herein, the matrix solution employs a saturated solution (10 mg/mL) in which CHCA (α-cyano-4-hydroxycinnamic acid) is dissolved by a mixed solution of water and acetonitrile, and the rinsing solution employs acetone, for example.

The matrix solution is fed through the tube 16 connected to the capillary 2 via a T-type three-way joint J1 by a pump 49, flowed outside the capillary 2, and dripped together with the eluate containing the sample constituents from the tip portion of the probe 1.

An air supply tube 24 and a rinsing solution supply tube 26 are joined by a T-type three-way joint J3, and a pipe 18 as a common flow passage is connected to the capillary 2 through which the eluate flows and the tube through which the matrix solution flows via a T-type three-way joint J2, whereby the air and rinsing solution flow further outside the tube through which the matrix solution flows. The rinsing solution employs acetone, for example.

A valve 28 is attached to the air supply tube 24, in which the supply of the air is controlled by opening and closing the valve 28. A pump 30 is provided in the rinsing solution supply tube 26, whereby the rinsing solution of acetone is supplied through the rinsing solution supply tube 26 into the probe 1 by operating the pump 30.

In dripping the eluate from the liquid chromatograph, the matrix solution is dripped, together with the eluate, from the tip portion of the probe 1 onto the sample plate S. After dripping the liquid, the matrix may deposit on the tip portion of the probe 1, whereby the rinsing solution of acetone is supplied through the rinsing solution supply tube 26 to the tip portion of the probe 1 to rinse the tip portion of the probe 1. To prevent the rinsing solution from remaining on the tip portion after rinsing the tip portion of the probe 1, the valve 28 is opened to supply the air to the tip portion of the probe 1 of the probe 1, and evaporate the rinsing solution remaining on the tip portion of the probe 1.

Figure 2:
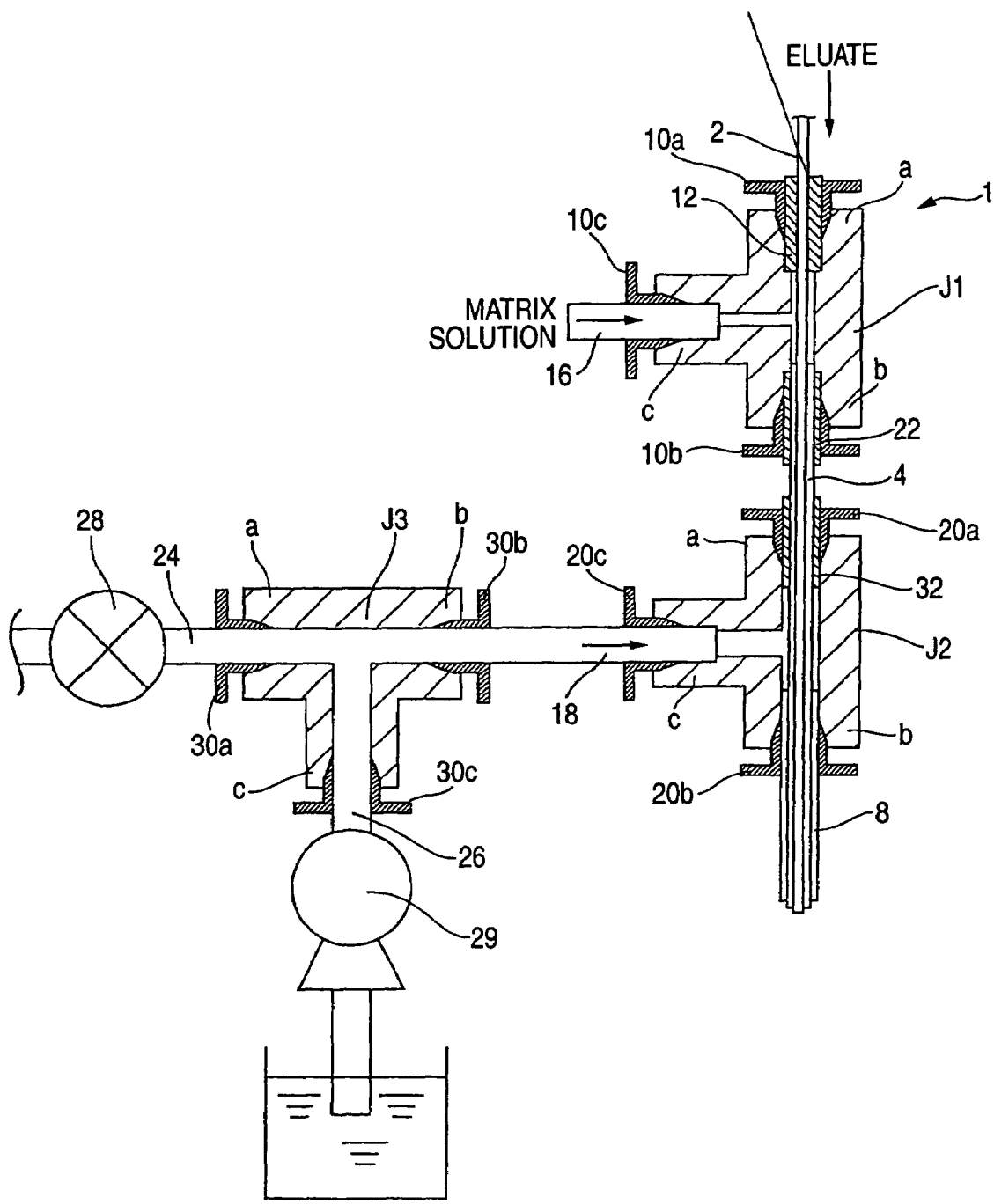
FIG. 2 is a longitudinal cross-sectional view showing in detail the structure of a probe in the embodiment.

FIG. 2 is a longitudinal cross-sectional view showing in detail the structure of a probe in the embodiment.

Two joints a and b, not orthogonal, of the first T-type three-way joint J1 on the upstream side are traversed by the slenderest capillary 2 through which the eluate from the high performance liquid chromatograph is fed. A joint a on the upstream side is tightly sealed via a sleeve 12 by a pipe fitting 10a such as a male nut. The capillary 2 employs the fused silica capillary.

An orthogonal joint c of the T-type three-way joint J1 is connected to the pipe 16 through which the matrix solution is fed, and tightly sealed by a pipe fitting 10c such as a male nut. In a joint b from which the slenderest capillary 2 extends, a capillary 4 is covered over the capillary 2 with a clearance, and tightly sealed via a sleeve 22 by a pipe fitting 10b such as a male nut. The capillary 4 employs an FEP tube.

The capillaries 2 and 4 are inserted into the T-type three-way joint J2 on the downstream side from a joint a on the upstream side, and tightly sealed via a sleeve 32 by a pipe fitting 20a such as a male nut. The joint c orthogonal to the capillaries 2 and 4 is connected to the tube 18 for supplying the air and the rinsing solution of acetone, and tightly sealed by a pipe fitting 20c such as a male nut. In a joint b on the most downstream side, a pipe 8 is covered over the capillaries 2 and 4 with a clearance, and tightly sealed by a pipe fitting 20b such as a male nut. The pipe 8 employs a stainless tube.

A distal end of the capillary 2 extends from the tip portion of the probe 1, in which the distal end position of the capillary 4 is retreated from the distal end of the capillary 2, and the distal end position of the pipe 8 is further retreated from the distal end of the capillary 4.

The air supply tube 24 from a joint a, the pipe 18 connected to the T-type three-way joint J2 from a joint b and the rinsing solution supply tube 26 from a joint c are inserted into the T-type three-way joint J3 located sideways of the T-type three-way joint J2, and tightly sealed by the pipe fittings 30a, 30b and 30c such as male nuts.

The air supply tube 24 is provided with the valve 28, whereby the supply of the air to the tip portion of the probe 1 is switched on or off by opening or closing the valve 28. The rinsing solution supply tube 26 is provided with the pump 29, whereby the supply of acetone through the pipe 18 to the tip portion of the probe 1 is switched on or off by turning on or off the operation of the pump 29.

In performing a fractionation operation, if the matrix has deposited at the tip portion of the probe 1 in the previous fractionation operation, the pump 29 is activated to supply acetone and dissolve and remove the matrix, and then deactivated, and the valve 28 is opened to feed the air to the tip portion of the probe 1 to evaporate residual acetone.

Thereafter, the eluate is supplied to the capillary 2 from the liquid chromatograph and the matrix is supplied to the capillary 4, whereby the sample liquid droplet is dripped and fractionated.

Usually, the HPLC used for fractionation analysis of a biosample is effected by a gradient method, in which the initial composition of a mobile phase has a low concentration of organic solvent, and the percentage of water is high as the constituent of the mobile phase. Because water has a great surface tension, there is the tendency that the liquid droplet emerging from the tip portion of the probe rises up the outside of the probe, if the percentage of water in the mobile phase is high.

As one criterion for assessing the hydrophobic and hydrophilic properties of the matter, a contact angle may be employed, in which the hydrophobic property is stronger with greater contact angle. The contact angle of PEEK is the greatest among the materials employed for the probe, or about 88°, and the contact angle of FEP is about 120°. In this embodiment, since the capillary 4 employs the FEP tube, the hydrophobic property is excellent, and the liquid droplet of the mixed solution of the eluate from the liquid chromatograph and the matrix liquid is less likely to pass outside of the capillary 4, and the uniform liquid droplet can be formed at the tip portion of the probe 1, whereby the liquid droplet makes contact with the sample plate when the stage is raised, and is uniformly fractionated on the sample plate.

Though in this embodiment, the liquid chromatograph has the probe of triple tube structure, the invention may be applied to the probes having other multiple tube structures than the triple tube structure or the single tube structure.

Also, as the tube for increasing the hydrophobic property, other fluororesin tubes may be employed, instead of the FEP tube of this embodiment, to achieve the same effects.

What is claimed is:

1. A fractionating apparatus comprising: a plate and a probe for dripping a sample liquid fed from a liquid feed mechanism as a liquid droplet from a tip portion of the probe onto the plate, wherein the tip portion of said probe comprises at least a double tube structure with a central tube for feeding the sample liquid and an additive agent supply tube coaxial with said central tube and disposed outside said central tube, wherein said additive agent supply tube is made of a hydrophobic material, and wherein the additive agent supply tube in contact with said liquid droplet is made of a hydrophobic material.

2. The fractionating apparatus according to claim 1, wherein said hydrophobic material is fluororesin.

3. The fractionating apparatus according to claim 1, wherein said liquid feed mechanism is a liquid chromatograph.

4. The fractionating apparatus according to claim 1, wherein the tip portion of said probe comprises a triple tube structure with a first tube for feeding the sample liquid, a second tube for supplying an additive agent and a third tube for supplying a rinsing solution or air, the second tube being coaxial with said first tube and disposed outside said first tube, the third tube being coaxial with said second tube and disposed outside said second tube, and wherein said second tube is made of a hydrophobic material.

* * * * *